United States Patent
Song et al.

(10) Patent No.: US 9,259,455 B2
(45) Date of Patent: Feb. 16, 2016

(54) CHEMICALLY MODIFIED CELLULOSE FIBROUS MESHES FOR USE AS TISSUE ENGINEERING SCAFFOLDS

(75) Inventors: Jie Song, Shrewsbury, MA (US); Tera Marie Filion Potts, West Boyston, MA (US); Artem Kutikov, Worcester, MA (US)

(73) Assignee: University of Massachusetts, Boston, MA (US)

( * ) Notice: Subject to any disclaimer, the term of this patent is extended or adjusted under 35 U.S.C. 154(b) by 52 days.

(21) Appl. No.: 13/438,094

(22) Filed: Apr. 3, 2012

(65) Prior Publication Data

US 2012/0258160 A1 Oct. 11, 2012

Related U.S. Application Data

(60) Provisional application No. 61/474,059, filed on Apr. 11, 2011.

(51) Int. Cl.

| | |
|---|---|
| *A61K 9/70* | (2006.01) |
| *A61K 38/18* | (2006.01) |
| *D01D 5/00* | (2006.01) |
| *D01F 2/28* | (2006.01) |
| *A61K 9/00* | (2006.01) |
| *A61K 47/38* | (2006.01) |
| *A61L 31/04* | (2006.01) |
| *C08L 1/12* | (2006.01) |
| *A61K 38/19* | (2006.01) |
| *A61K 38/30* | (2006.01) |
| *D06M 13/262* | (2006.01) |
| *D06M 13/342* | (2006.01) |
| *D06M 13/368* | (2006.01) |
| *D06M 13/372* | (2006.01) |
| *D01D 10/02* | (2006.01) |
| *D01F 11/02* | (2006.01) |
| *D06M 101/06* | (2006.01) |

(52) U.S. Cl.
CPC ........... *A61K 38/1841* (2013.01); *A61K 9/0024* (2013.01); *A61K 9/70* (2013.01); *A61K 38/18* (2013.01); *A61K 38/1825* (2013.01); *A61K 38/1866* (2013.01); *A61K 38/1875* (2013.01); *A61K 38/191* (2013.01); *A61K 38/30* (2013.01); *A61K 47/38* (2013.01); *A61L 31/04* (2013.01); *C08L 1/12* (2013.01); *D01D 5/003* (2013.01); *D01D 10/02* (2013.01); *D01F 2/28* (2013.01); *D01F 11/02* (2013.01); *D06M 13/262* (2013.01); *D06M 13/342* (2013.01); *D06M 13/368* (2013.01); *D06M 13/372* (2013.01); *D06M 2101/06* (2013.01)

(58) Field of Classification Search
None
See application file for complete search history.

(56) References Cited

U.S. PATENT DOCUMENTS

| | | | | |
|---|---|---|---|---|
| 5,972,385 | A | * 10/1999 | Liu et al. | 424/486 |
| 2007/0275458 | A1 | * 11/2007 | Gouma | 435/297.4 |
| 2010/0216211 | A1 | * 8/2010 | Shauer et al. | 435/183 |

OTHER PUBLICATIONS

Ma, Z. and J. Song, "Chondrogenic electrospun polyelectrolyte fiber meshes," Abstracts of Papers, 234th ACS National Meeting, Aug. 19-23, 2007.*
Ma, Z. and S. Ramakrishna, "Electrospun regenerated cellulose nanofiber affinity membrane functionalized with protein A/G for IgG purification," Journal of Membrane Science 319: 23-28 (2008).*
Sangsonah, P., et al, "In vitro biocompatibility of electrospun and solvent-cast chitosan substrata toward Schwann, osteoblast, keratinocyte and fibroblast cells," European Polymer Journal 46: 428-440 (available online Nov. 4, 2009).*
Gouma, P.-I., et al., "Novel Biooceramics for Bone Implants," Advances in Bioceramics and Porous Ceramics II, Presented at the 33rd International Conference on Advanced Ceramics and Composites, Jan. 18-23, 2009, pp. 35-44.*

* cited by examiner

*Primary Examiner* — David J Blanchard
*Assistant Examiner* — Daniel F Coughlin
(74) *Attorney, Agent, or Firm* — Milstein Zhang & Wu LLC

(57) ABSTRACT

Cellulose and sulfated cellulose fibrous meshes exhibiting robust structural and mechanical integrity in water were fabricated using a combination of electrospinning, thermal-mechanical annealing and chemical modifications. The sulfated fibrous mesh exhibited higher retention capacity for human recombinant bone morphogenetic protein-2 than the cellulose mesh, and the retained proteins remained biologically active for at least 7 days. The sulfated fibrous mesh also more readily supported the attachment and osteogenic differentiation of rat bone marrow stromal cells in the absence of osteogenic growth factors. These properties combined make the sulfated cellulose fibrous mesh a promising bone tissue engineering scaffold.

10 Claims, 9 Drawing Sheets

Lung　　　　　　　　　Heart　　　　　　　　Kidney

Spleen　　　　　　Bone marrow (rib)　　　　Liver

CHEMICALLY MODIFIED CELLULOSE FIBROUS MESHES FOR USE AS TISSUE ENGINEERING SCAFFOLDS

PRIORITY CLAIMS AND CROSS REFERENCE TO RELATED APPLICATIONS

This application claims the benefit of priority from U.S. Provisional Application Ser. No. 61/474,059, filed Apr. 11, 2011, the entire content of which is incorporated herein by reference in its entirety.

GOVERNMENT RIGHTS

This invention was made with Government support under Grant No. W81XWH-10-0574 awarded by the US Department of Defense. The Government has certain rights in the invention.

TECHNICAL FIELD OF THE INVENTION

The invention generally relates to novel fibrous meshes and related methods of preparation and use. More particularly, the invention relates to unique chemically modified cellulose fibrous meshes that are useful in tissue engineering applications, such as serving as tissue scaffolds and drug-delivery membranes.

BACKGROUND OF THE INVENTION

Electrospinning uses an electrical charge to draw fine (typically on the micro or nano scale) fibres from a liquid. It is a robust technique for fabricating polymer fibrous meshes mimicking the extracellular matrices (ECM) of natural tissues. (Pham, et al. 2006 *Tissue Engineering* 12, (5), 1197-1211.) Electrospinning shares characteristics of both electrospraying and conventional solution dry spinning of fibers. By adjusting the viscosity and surface tension of the polymer solution as well as the voltage, speed and duration of the electrospinning process, polymer fibrous meshes of varied fiber dimensions and mesh thicknesses and porosities could be obtained. (Huang, et al. 2003 *Composites Science and Technology* 63 (15), 2223-2253; Li, et al. 2004 *Advanced Materials* 16 (14), 1151-1170.) For in vivo tissue engineering applications, however, these fibrous meshes should also be engineered with proper biochemical microenvironment (e.g., via the retention of tissue-specific biological cues) to help support cellular attachment, direct stem cell differentiation, and guide tissue integration.

Covalent modification of synthetic scaffolds with growth factors was previously attempted for expediting bone tissue repair. (Uludag, et al. 2000 *Biotechnol. Prog.* 16 (2), 258-267; Gittens, et al. 2004 *Journal of Controlled Release* 98 (2), 255-268.) This approach, however, risks compromising the bioactivity of the proteins due to substantial structural perturbation. (Katagiri, et al. 1994 *Journal of Cell Biology* 127 (6), 1755-1766; Uludag, et al. 1999 *Biotechnol. Bioeng.* 65 (6), 668-672.) By contrast, strategies for retaining protein therapeutics through non-covalent electrostatic interactions are more biomimetic in nature. For instance, sulfated polysaccharides are known for their high affinity for many endogenous proteins within the ECM environment such as various isoforms of bone morphogenetic proteins (BMPs), presumably through favorable electrostatic interactions between the sulfate residues and the basic amino acid residues of the proteins. (Vukicevic, et al. 1994 *Biochem. Biophys. Res. Commun.* 198 (2), 693-700; Irie, et al. 2003 *Biochem. Biophys. Res. Commun.* 308 (4), 858-865; Ruppert, et al. 1996 *Eur. J. Biochem.* 237, (1), 295-302; Takada, et al. 2003 *Journal of Biological Chemistry* 278, (44), 43229-43235.) Such biopolymers are ideal candidates for the fabrication of synthetic tissue scaffolds. Indeed, chondroitin sulfate, an important sulfated structural component of cartilage tissue, has been shown to enhance bone remodeling of musculoskeletal defects when used in combination with other bone grafting materials. (Schneiders, et al. 2008 *Journal of Orthopaedic Research*, DOI 10.1002/jor.20719.) The application of electrospun chondroitin sulfate fibrous meshes to augment the performance of 3-dimensional tissue engineered constructs, however, has proven challenging due to their exceptionally high solubility in water. In our hands, for example, methacrylating chondroitin sulfate with glycidyl methacrylate (Li, et al. 2004 *Journal of Biomedical Materials Research Part A* 68A (1), 28-33.) prior to electrospinning, followed by covalent crosslinking of the electrospun meshes, failed to improve the stability of the mesh in water.

Thus, an urgent unmet need remains for combining suitable polymers with practical fabrication methods to prepare biocompatible synthetic tissue scaffolds.

SUMMARY OF THE INVENTION

The invention provides novel methods for preparing water-stable sulfated polysaccharide fibrous meshes from readily accessible electrospun cellulose acetate. The sulfated cellulose fibrous meshes of the invention exhibit robust structural and mechanical integrity in water and can be fabricated by electrospinning, thermal-mechanical annealing and chemical modifications. The sulfated fibrous mesh exhibit high retention capacities for various proteins, such as human recombinant bone morphogenetic protein-2 and readily support the attachment and differentiation of various cells, such as rat bone marrow stromal cells and their osteogenic differentiation. These properties combined make the sulfated cellulose fibrous mesh a promising bone tissue engineering scaffold.

In one aspect, the invention generally relates to a method for preparing water-stable fibrous meshes. The method includes: electrospinning cellulose acetate to form cellulose acetate meshes; thermal-mechanically annealing the electrospun cellulose acetate meshes; and chemically modifying the annealed cellulose acetate meshes.

In some preferred embodiments, chemically modifying the annealed cellulose meshes includes: deacetylating the annealed cellulose meshes; oxidizing the deacetylated cellulose meshes to obtain aldehyde reactive functionalities; and reacting the oxidized cellulose meshes with an amino-sulfate to obtain sulfated cellulose meshes.

In another aspect, the invention generally relates to a fibrous mesh of thermal-mechanically annealed and subsequently sulfated cellulose.

In certain preferred embodiments, the fibrous mesh have thicknesses from about 10 µm to about 500 µm (e.g., about 10 µm, 20 µm, 50 µm, 100 µm, 150 µm, 200 µm, 250 µm, 300 µm, 350 µm, 400 µm, 450 µm, 500 µm) and comprise fibers from about 100 nm to about 20 µm in fiber diameter (e.g., about 100 nm, 250 nm, 500 nm, 750 nm, 1 µm, 2 µm, 3 µm, 4 µm, 5 µm, 6 µm, 7 µm, 8 µm, 9 µm, 10 µm, 12 µm, 15 µm, 20 µm in fiber diameter).

In yet another aspect, the invention generally relates to a biocompatible mesh composition. The mesh composition includes: fibrous sulfated cellulose, wherein the sulfated cellulose was obtained from thermal-mechanically annealed and subsequently chemically modified cellulose acetate; and a therapeutic material absorbed on the fibrous sulfated cellulose.

In certain preferred embodiments, the therapeutic material comprises an osteogenic growth factor, for example, a human bone morphogenetic protein (BMP) such as a natural or recombinant human BMP-1, BMP-2, BMP-3, BMP-4, BMP-5, BMP-6, BMP-7, BMP-8a, BMP-8b, BMP-10 or BMP-15. In certain preferred embodiments, the therapeutic material comprises a bone marrow stromal cell (MSC).

In certain preferred embodiments, the thermal-mechanically annealed and subsequently chemically modified cellulose acetate is obtained by: electrospinning cellulose acetate to form cellulose acetate mesh; thermal-mechanically annealing the electrospun cellulose acetate mesh; deacetylating the annealed cellulose mesh; oxidizing the deacetylated cellulose mesh to obtain aldehyde reactive functionalities; and reacting the oxidized cellulose mesh with an amino-sulfate to obtain sulfated cellulose meshes.

In yet another aspect, the invention generally relates to a water-stable biocompatible fibrous mesh that is prepared by a process including the steps of: (1) electrospinning cellulose acetate to form cellulose acetate meshes; (2) thermal-mechanically annealing the electrospun cellulose acetate meshes; and (3) chemically modifying the annealed cellulose acetate meshes. In certain preferred embodiments, chemically modifying the annealed cellulose meshes includes: deacetylating the annealed cellulose meshes; oxidizing the deacetylated cellulose meshes to obtain aldehyde reactive functionalities; and reacting the oxidized cellulose meshes with an amino-sulfate to obtain sulfated cellulose meshes.

The invention also relates generally to an implant device comprising the biocompatible mesh of the invention, for example, a scaffold-assisted repair device for bony defects seeded with bone marrow stromal cells or a BMP protein. The materials of the invention can also be used as skin grafts, or membranes wrapped around any other tissues as drug delivery vehicles.

DETAILED DESCRIPTION OF THE INVENTION

Figure 1:
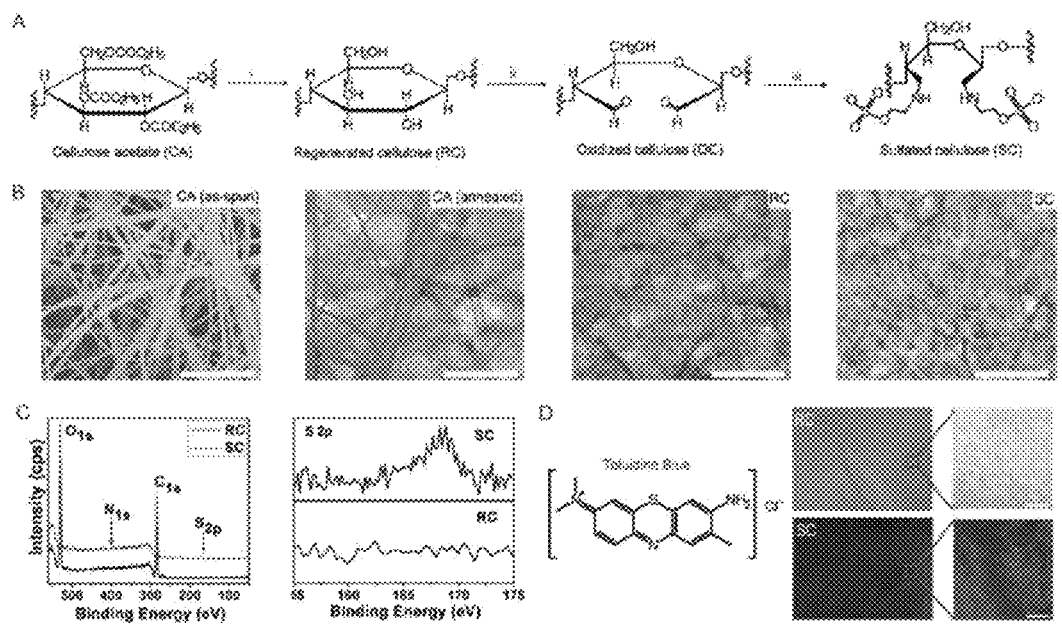
FIG. 1 shows: (A) Synthetic scheme for chemical modification of thermal-mechanically annealed CA mesh. i) NaOH (0.1 N, 1:4/EtOH:$H_2O$), rt, 12 h; ii) $NaIO_4$ (5 mg/mL, PBS), rt, 10 h; iii) 2-aminoethyl sulfate (0.05 g/mL, PBS), $NaBH_3CN$ (2.5 mg/mL, PBS), pH 7.4, rt, 12 h. All meshes were gently shaken on an orbital shaker during the chemical treatment and extensively washed in MilliQ water afterwards. (B) SEM micrographs of as-spun, thermal-mechanically annealed, and chemically modified meshes. Scale bars=40 μm. (C) X-ray photoelectron spectroscopy scans of the RC and SC meshes. D) Optical micrographs of RC and SC meshes after being immersed in an aqueous solution of toluidine blue (4 wt %) for 1 min and thoroughly rinsed in MilliQ water. Scale bars=500 μm.

The invention is based, in part, on a novel, practical method for preparing water-stable sulfated polysaccharide fibrous meshes from readily accessible electrospun cellulose acetate. For example, the invention provides sulfated cellulose meshes that exhibit robust structural and mechanical integrity in water, for example, superior elasticity and tensile strength. The sulfated cellulose meshes can be fabricated using a combination of electrospinning, thermal-mechanical annealing and chemical modifications. These meshes provide high retention capacities for various proteins, such as human recombinant bone morphogenetic protein-2 that remains biologically active for a number of days. The sulfated cellulose fibrous meshes also readily support the attachment and differentiation of various cells, such as rat bone marrow stromal cells and their osteogenic differentiation. These meshes are biocompatible, making them good candidates for use in tissue engineering applications, for example, as tissue scaffold materials.

Cellulose is an organic compound with the formula $(C_6H_{10}O_5)_n$, a polysaccharide consisting of a linear chain of several hundred to over ten thousand β (1→4) linked D-glucose units. Cellulose is a straight chain polymer derived from D-glucose units, which condense through β (1→4)-glycosidic bonds. Cellulose may have different chain length, for example, between 300 and 1700 units (from wood pulp) and from 800 to 10,000 units (cotton and other plant fibers). Cellulose acetate (also known as zyl or zylonite) is the acetate ester of cellulose. Cellulose acetate fibers are synthetic fibers in which the fiber-forming substance is cellulose acetate and are typically based on cotton or tree pulp cellulose.

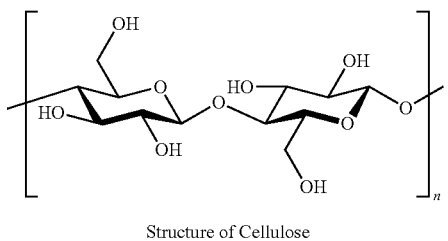

Structure of Cellulose

Cellulose is chosen as the candidate for sequential chemical modifications because it is an affordable natural polysaccharide known for its abundance, aqueous stability, cytocompatibility, and chemical functionalizability. (Hansson, et al. 2009 *Acs Applied Materials & Interfaces* 1 (11), 2651-2659; Kriegel, et al. 2008 *Critical Reviews in Food Science and Nutrition* 48 (8), 775-797.)

In one aspect, the invention generally relates to a method for preparing water-stable fibrous meshes. The method includes: electrospinning cellulose acetate to form cellulose acetate meshes; thermal-mechanically annealing the electrospun cellulose acetate meshes; and chemically modifying the annealed cellulose acetate meshes.

In some preferred embodiments, chemically modifying the annealed cellulose meshes includes: deacetylating the annealed cellulose meshes; oxidizing the deacetylated cellulose meshes to obtain aldehyde reactive functionalities; and reacting the oxidized cellulose meshes with an amino-sulfate to obtain sulfated cellulose meshes.

In certain embodiments, deacetylation is conducted in an aqueous base to regenerate cellulose. The aqueous base may be an inorganic or an organic base. In some embodiments, the inorganic base is NaOH or KOH in a alcohol:$H_2O$ (e.g., EtOH:$H_2O$) solution.

In certain embodiments, the oxidation is conducted with a periodate as the oxidant, for example, $NaIO_4$.

The amino-sulfate may be any amino-sulfate, for example, wherein the number of carbon atoms between the amino group and the sulfate group is from about 1 to about 16 (e.g., C1, C2, C3, C4, C6, C8, C10, C12, C16), and may be substituted or unsubstituted, linear, branched, or cyclic. In certain preferred embodiments, the amino-sulfate is 2-aminoethyl sulfate.

In certain preferred embodiments, the electrospun cellulose acetate mesh have thicknesses from about 200 μm to about 1,000 μm (e.g., about 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm in thickness) and comprise fibers from about 100 nm to about 50 μm in fiber diameter (e.g., about 100 nm, 250 nm, 500 nm, 750 nm, 1 μm, 3 μm, 5 μm, 7 μm, 10 μm, 12 μm, 15 μm, 20 μm, 25 μm, 30 μm, 35 μm, 40 μm, 45 μm, 50 μm in fiber diameter).

The thermal-mechanical annealing may be performed under a pressure ranging from about 1 MPa to about 500 MPa (e.g., about 1 MPa, 2 MPa, 5 MPa, 10 MPa, 15 MPa, 20 MPa, 25 MPa, 30 MPa, 35 MPa, 40 MPa, 45 MPa, 50 MPa, 100 MPa, 200 MPa, 500 MPa). The thermal-mechanical annealing may be performed at a temperature ranging from about room temperature to about 240° C. (e.g., about 25° C., 30° C., 35° C., 40° C., 45° C., 50° C., 55° C., 60° C., 65° C., 70° C., 75° C., 80° C., 85° C., 90° C., 100° C., 120° C., 140° C., 160° C., 180° C., 200° C., 220° C., 240° C.). A step-wise procedure may be used such that the thermal-mechanical annealing is performed at stepped temperature and/or pressure to optimally achieve the desired outcome.

In some embodiments, the thermal-mechanically annealed cellulose acetate mesh have fibers having dimensions from about 10 μm to about 500 μm in thickness (e.g., about 10 μm, 20 μm, 50 μm, 100 μm, 150 μm, 200 μm, 250 μm, 300 μm, 350 μm, 400 μm, 450 μm, 500 μm). The chemically modified cellulose mesh may have fibers having an elastic modulus from about 0.1 MPa to about 100 MPa (e.g., about 0.2 MPa, 0.5 MPa, 1 MPa, 2 MPa, 5 MPa, 10 MPa, 15 MPa, 20 MPa). As used herein, elastic modulus is defined as the slope of the tensile stress-strain curve in the elastic deformation region.

In another aspect, the invention generally relates to a fibrous mesh of thermal-mechanically annealed and subsequently sulfated cellulose.

In certain preferred embodiments, the fibrous mesh have fibers having dimensions from about 10 μm to about 500 μm in thickness (e.g., from about 10 μm to about 100 μm) and from about 100 nm to about 20 μm in fiber diameter (e.g., about 100 nm, 250 nm, 500 nm, 750 nm, 1 μm, 2 μm, 3 μm, 4 μm, 5 μm, 6 μm, 7 μm, 8 μm, 9 μm, 10 μm, 12 μm, 15 μm, 20 μm in fiber diameter).

In some embodiments, the fibrous mesh may have fibers having an ultimate tensile strength from about 50 KPa to about 50 MPa (e.g., about 100 KPa, 200 KPa, 500 KPa, 1 MPa, 2 MPa, 5 MPa, 10 MPa, 20 MPa, 30 MPa, 50 MPa). As used herein, ultimate tensile strength is defined as the maximum tensile stress at the break.

In yet another aspect, the invention generally relates to a biocompatible mesh composition. The mesh composition includes: fibrous sulfated cellulose, wherein the sulfated cellulose was obtained from thermal-mechanically annealed and subsequently chemically modified cellulose acetate; and a therapeutic material absorbed on the fibrous sulfated cellulose.

In certain preferred embodiments, the therapeutic material comprises an osteogenic growth factor, for example, a human bone morphogenetic protein (BMP) such as a natural or recombinant human BMP-1, BMP-2, BMP-3, BMP-4, BMP-5, BMP-6, BMP-7, BMP-8a, BMP-8b, BMP-10 or BMP-15. The osteogenic growth factor may be present in the range from about 1 ng/$cm^2$ to about 100 μg/$cm^2$ (e.g., about 100 ng/cm$^2$, 500 ng/cm$^2$, 1 µg/cm$^2$, 3 µg/cm$^2$, 5 µg/cm$^2$, 10 µg/cm$^2$). Preferably, the osteogenic growth factor is present in the range from about 10 ng/cm$^2$ to about 10 µg/cm$^2$ (e.g., 10 ng/cm$^2$, 20 ng/cm$^2$, 30 ng/cm$^2$, 40 ng/cm$^2$, 50 ng/cm$^2$, 60 ng/cm$^2$, 70 ng/cm$^2$, 80 ng/cm$^2$, 90 ng/cm$^2$, 100 ng/cm$^2$, 400 ng/cm$^2$, 1.5 µg/cm$^2$, 3 µg/cm$^2$, 5 µg/cm$^2$, 10 µg/cm$^2$). The sulfated fibrous mesh of the invention provides high retention capacities for various proteins and cells, such as human recombinant bone morphogenetic protein-2 that remains biologically active for a number of days (e.g., greater than 1 day, 3 days, 5 days, 7 days, 10 days, 14 days, 21 days). Other therapeutic agents include, but not limited to, various isoforms of recombinant proteins VEGF, IGF, TGFbeta, FGF, RANKL, TNFalpha, SDF, etc.

In certain preferred embodiments, the therapeutic material comprises a bone marrow stromal cell (MSC). The bone marrow stromal cell is present in the range from about 1000 to about 10,000,000 cells/cm$^2$ (e.g., about 5,000 cells/cm$^2$, 10,000 cells/cm$^2$, 100,000 cells/cm$^2$, 500,000 cells/cm$^2$, 1,000,000 cells/cm$^2$, 5,000,000 cells/cm$^2$, 10,000,000 cells/cm$^2$). Preferably, the bone marrow stromal cell is present in the range from about 10,000 to about 1,000,000 cells/cm$^2$ (e.g., 20,000 cells/cm$^2$, 50,000 cells/cm$^2$, 100,000 cells/cm$^2$, 200,000 cells/cm$^2$, 500,000 cells/cm$^2$, 1,000,000 cells/cm$^2$). Hematopoietic stem cells (HSCs), and other primary cells such as endothelial cells, fibroblasts, osteoblasts, myoblasts, chondrocytes, may also be used with the biocompatible meshes of the invention.

In certain preferred embodiments, the thermal-mechanically annealed and subsequently chemically modified cellulose acetate is obtained by: electrospinning cellulose acetate to form cellulose acetate mesh; thermal-mechanically annealing the electrospun cellulose acetate mesh; deacetylating the annealed cellulose mesh; oxidizing the deacetylated cellulose mesh to obtain aldehyde reactive functionalities; and reacting the oxidized cellulose mesh with an amino-sulfate to obtain sulfated cellulose meshes.

The invention also relates generally to an implant device comprising the biocompatible mesh of the invention, for example, a scaffold-assisted repair device for bony defects seeded with bone marrow stromal cells or a BMP protein. The materials of the invention may also be used as skin grafts, or membranes wrapped around any other tissues as drug delivery vehicles.

EXAMPLES

Example 1

FIG. 1A illustrates an embodiment of the invention, showing the synthetic scheme for chemical modification of thermal-mechanically annealed cellulose acetate (CA) mesh. Since cellulose itself is not soluble in most organic solvents, thus unsuitable for electrospinning, water-stable sulfated polysaccharide fibrous meshes may be prepared from readily accessible electrospun cellulose acetate. CA fibrous mesh was first electrospun by ejecting 2,2,2-trifluoroethanol solution of CA (150 g/L) at a rate of 2.4 mL/h under 15 kV with a distance of 10 cm between the ejection tip and the collection plate. After 4 h of electrospining, CA fibrous meshes 400-650 µm in thickness and with fiber diameters ranging from several hundred nanometers to a few micrometers were obtained (FIG. 1B).

The electrospun meshes were then thermal-mechanically annealed to sustain sequential chemical modifications and to exhibit adequate tensile modulus for use as a flexible 2-dimensional tissue engineering scaffold (e.g. to be wrapped around 3-dimensional tissue grafts or embedded within a tissue defect).

Figure 5:
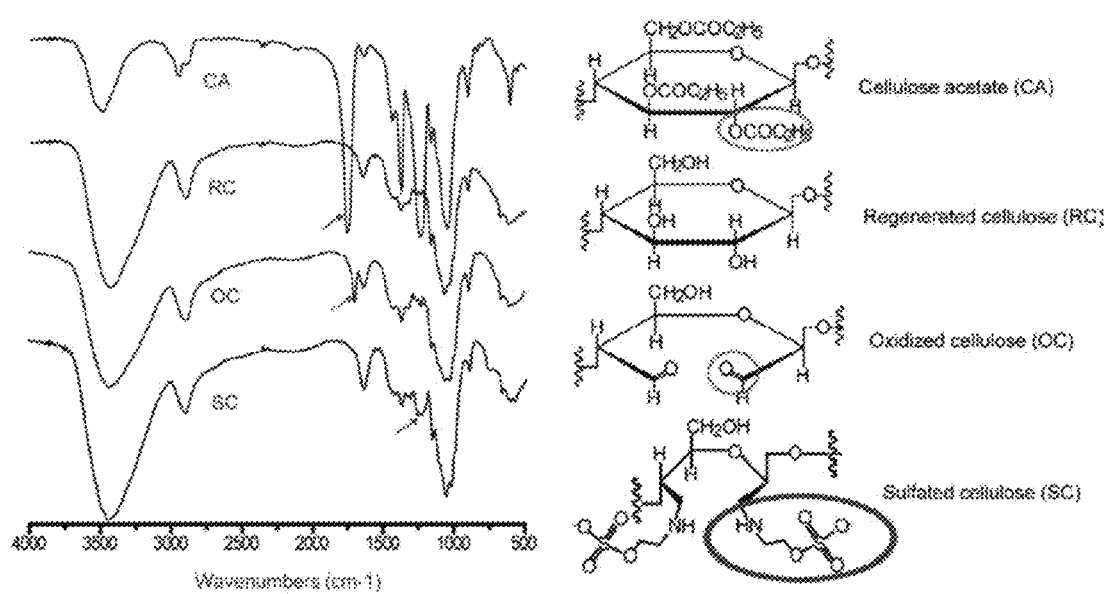
FIG. 5 shows: Fourier transform infrared spectroscopy (FTIR) supporting sequential chemical modifications. FTIR characterization of the regenerated cellulose (RC) mesh supported the complete removal of the acetyl groups (green arrow) from the cellulose acetate (CA) mesh upon base hydrolysis. The oxidized cellulose (OC) mesh exhibited a characteristic FTIR absorption at 1700 $cm^{-1}$ corresponding to the aldehyde functionality (red arrow). After reductive amination with 2-aminoethyl sulfate, the sulfated cellulose (SC) mesh exhibited signals corresponding to aminoethyl sulfate (blue arrow).

The as-spun CA meshes were cut into 2" by 2" square pieces and annealed on a Carver hydraulic hot press under 25.85-MPa compressive loading for 10 min at either room temperature or 90° C., which was >20° C. above the glass transition temperature of CA and chosen to enhance the physical bonding of the CA fibers. (Han, et al. 1995 *Desalination* 101 (2), 195-200.) The final thicknesses of the mechanically and thermal-mechanically annealed CA meshes were approximately 100 µm and 60 µm, respectively, SEM micrographs (FIG. 1B) confirmed that whereas the fiber dimensions remained unchanged upon thermal-mechanical annealing, the annealed mesh exhibited denser packing between fibrous layers. The annealed CA mesh was then deacetylated in aqueous base (FIG. 1A) to yield regenerated cellulose (RC), which was further oxidized by sodium periodate to obtain the aldehyde reactive handles for coupling with 2-aminoethyl sulfate under reductive amination conditions to generate the sulfated cellulose (SC) mesh. The complete deacetylation of the CA mesh and the subsequent oxidation and reductive amination were monitored and verified by Fourier transform infrared spectroscopy (FIG. 5). X-ray photoelectron spectroscopy analysis performed on the SC mesh detected the S and N signals that were absent from the RC mesh (FIG. 1C). The sulfated mesh was also readily stained by positively charged toluidine blue dye, which is commonly used for the histochemical detection of sulfated glycosaminoglycans in cartilage. By contrast, only a minimal amount of toluidine blue was absorbed on the uncharged RC mesh. Overall, these findings support successful sequential chemical modifications. The average thickness of RC mesh obtained from the mechanically compressed CA mesh was 103±6 µm, and the average thicknesses of the RC and SC meshes obtained from the thermal-mechanically annealed CA mesh were 65±5 µm and 58±5 µm, respectively, supporting minimal thinning resulting from the chemical modifications. SEM micrographs (FIG. 1B) revealed some degree of narrowing of the fiber diameters upon chemical treatment, although the overall packing density between fibrous layers of the RC and SC meshes were comparable to that of the thermal-mechanically annealed CA mesh.

Example 2

Figure 2:
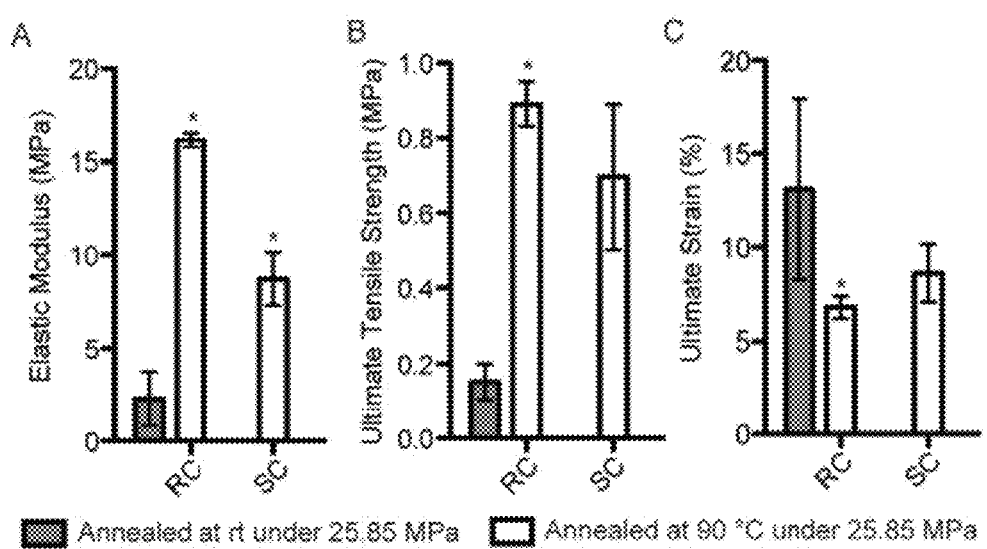
FIG. 2 shows: (A) Tensile elastic modulus, (B) ultimate tensile strength, and (C) ultimate tensile strain of hydrated RC and SC meshes as a function of annealing conditions. All testing was performed at rt on a Q800 dynamic mechanical analyzer (TA Instruments) equipped with a tensile submersion fixture filled with MilliQ water. Specimens (6-mm wide, 15-mm long, N=3) were preloaded with a tensile force of 0.01 N and ramped to failure at a rate of 0.1 N/min. Elastic modulus was calculated as the slope of the linear region of the stress-strain curve. Ultimate tensile strength and ultimate tensile strain were determined as the maximum stress and maximum strain at break, respectively. Error bars indicate standard deviation; * indicates $P<0.05$ as determined by Student's t-test.

Tensile mechanical testing of the meshes in hydrated state (FIG. 2) show that thermal-mechanical annealing is superior to mechanical compression alone for mesh processing. The RC mesh obtained from thermal-mechanically annealed CA exhibited significantly higher elastic modulus and ultimate tensile strength (~500% increases, $p<0.05$) than those obtained from the mechanically compressed mesh. Without prior thermal-mechanical annealing, the SC mesh obtained after multi-step chemical modifications was not robust enough to withstand tensile mechanical testing. By contrast, the SC mesh functionalized from thermal-mechanically annealed CA mesh maintained megapascal-elastic modulus and ultimate tensile strength in water. The thermal-mechanically annealed RC and SC meshes also exhibited >5% ultimate tensile strains. Overall, these meshes exhibit promising mechanical integrity for flexible manipulations as tissue engineering scaffolds (e.g. wrapping around a 3-dimensional scaffold, press-fitting in an area of defect, or covering an open wound surface with minor stretching).

The ability of the sulfated fibrous meshes to retain human recombinant bone morphogenetic protein-2 (rhBMP-2) and to support the in vitro attachment and osteogenic differentiation of bone marrow stromal cells (MSCs) for potential bone tissue engineering applications were examined and compared with those of the uncharged cellulose meshes.

Example 3

Figure 3:
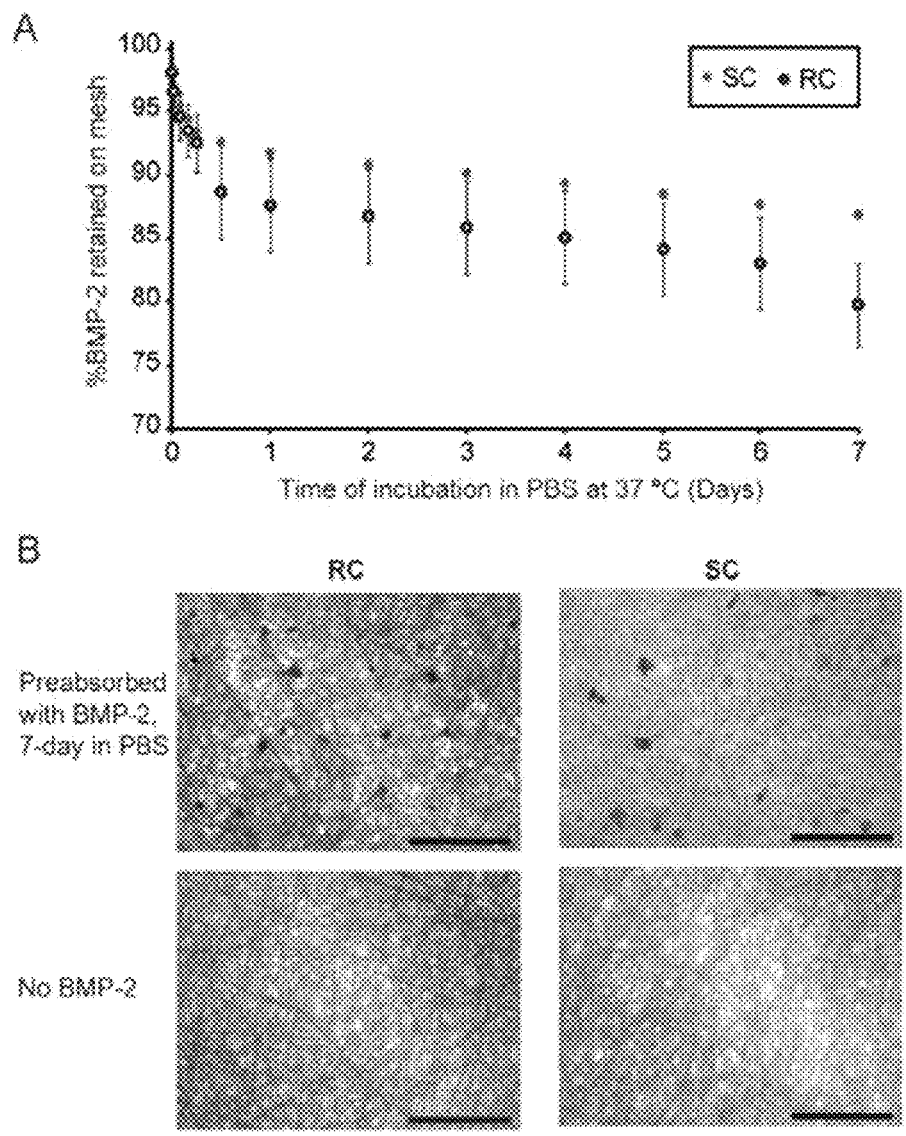
FIG. 3 shows: (A) Retention/release profile of rhBMP-2 on/from SC vs. RC meshes. The mesh (N=3) was pre-absorbed with rhBMP-2 (27 ng/$cm^2$) and air-dried before being incubated in PBS at 37° C. for 7 days. The protein released in PBS at a given time was quantified by ELISA. (B) Bioactivity of the rhBMP-2 retained on the mesh after 7-day incubation in PBS as indicated by their ability to induce osteogenic transdifferentiation of myoblast C2C12 cells. C2C12 cells were seeded (10,000 cells/$cm^2$) on either BMP-2 treated meshes retrieved after 7-day incubation in PBS (top) or those without rhBMP-2 treatment (bottom), and cultured in DMEM with 10% FBS without additional supplement of BMP-2. Alkaline phosphatase staining (red) was performed on day 3 of the culture. Scale bars=200 μm.

To examine the ability of RC and SC fibrous meshes to retain/release protein therapeutics, the meshes were absorbed with a single dose of rhBMP-2 (R&D Systems, pI=9.3, 27-ng/cm$^2$) and incubated in PBS at 37° C. for 7 days. The rhBMP-2 released from the meshes over time was quantified by an enzyme-linked immunosorbent assay (ELISA, R&D Systems). As shown in FIG. 3A, both meshes released pre-absorbed rhBMP-2 in a sustained manner over 7 days. The SC mesh exhibited better retention of rhBMP-2 than the RC mesh, with >85% of the protein still retained on the sulfated mesh after 7 days. More importantly, the rhBMP-2 retained on both RC and SC meshes remained biologically active, as evidenced by their ability to induce the osteogenic transdifferentiation of myoblast C2C12 cells in culture. In the absence of rhBMP-2, C2C12 cells cultured on RC and SC meshes did not express osteogenic marker alkaline phosphatase (FIG. 3B, bottom). However, when they were seeded on the BMP-treated meshes retrieved after 7-day incubation in PBS, the expression of alkaline phosphatase (stained red) was detected on day 3 of the culture (FIG. 3B, top), supporting the osteoinductity of the recombinant protein retained on the meshes. (Katagiri, et al. 1994 *Journal of Cell Biology* 127 (6), 1755-1766.)

Example 4

Figure 4:
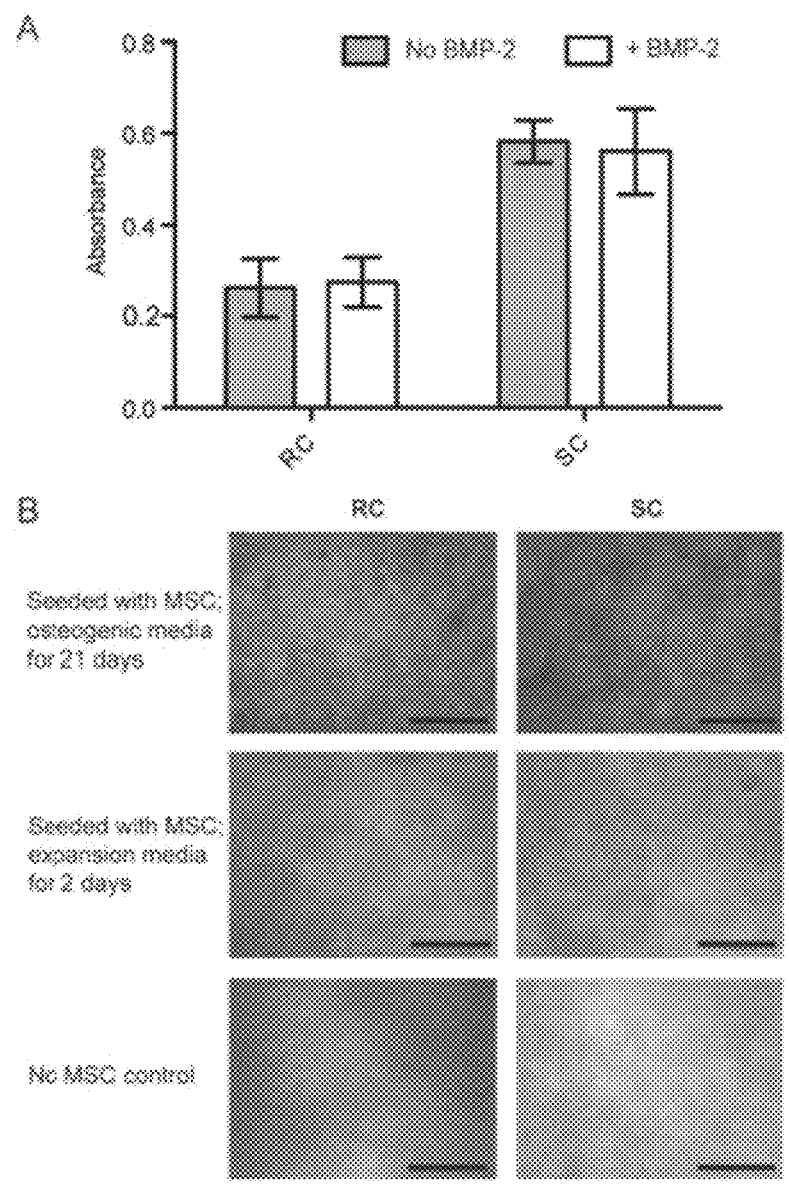
FIG. 4 shows: (A) MTT cell viability assay performed 48 h after seeding rat MSCs on the RC and SC meshes with and without pre-absorbed rhBMP-2 in expansion media. (B) Alizarin red staining of the MSCs cultured on RC and SC meshes in osteogenic differentiation media for 21 days (top) or in expansion media for 2 days (middle). Control meshes without cells were also stained (bottom). Scale bars=200 μm. All meshes were equilibrated in PBS for 1 h prior to cell seeding. Seeding density for all experiments was 25,000 cells/$cm^2$.

To assess the suitability of these fibrous meshes for bone tissue engineering applications, the ability of RC and SC meshes to support the attachment and osteogenic differentiation of rat bone marrow stromal cells (MSCs) were examined in culture. MSCs have the ability to differentiate into multiple lineages of the mesenchyme including osteoblasts, and have been widely used for scaffold-assisted repair of bony defects. (Caplan, et al. 1991 *Journal of Orthopaedic Research* 9 (5), 641-650; Friedenstein, et al. 1976 *Experimental Hematology* 4 (5), 267-274; Prockop 1997 *Science* 276 (5309), 71-74.) Total bone marrow was isolated from the long bone of an 8-week old male Charles River SASCO SD rat and the MSCs were established through adherent culture and expanded as previously described. (Song, et al. 2009 *Journal of Biomedical Materials Research Part A* 89A (4), 1098-1107.) Passage 1 MSCs were seeded on RC and SC meshes (25,000 cells/cm$^2$) with and without pre-absorbed rhBMP-2 (27-ng/cm$^2$) and allowed to attach in expansion media (αMEM without ascorbic acid, 20% FBS). MTT cell viability assay (FIG. 4A) performed 48 h after the initial cell seeding showed that significantly more viable cells (>100% increase) were attached to the SC mesh than to the uncharged RC mesh, and that the absorption of rhBMP-2 on the meshes prior to cell seeding had little effect on the cellular attachment/early proliferation. To examine whether or not the intrinsic osteogenic differentiation potential of MSCs was retained upon being attached to the fibrous meshes for 2 days, the MSC-seeded RC and SC meshes (without prior rhBMP-2 absorption) were continually cultured in osteogenic differentiation media (αMEM with L-glutamine, 15% FBS, 10 nM dexamethasone, 20 mM β-glycerol phosphate, 50 µM 1-ascorbic acid 2-phosphate) for 3 weeks, with the osteogenic media changed every 2 to 3 days. Alizarin red staining was performed on day 21 for the detection of mineralized matrix deposition resulting from osteogenic differentiation of MSCs. As shown in FIG. 4B, both RC and SC meshes were able to support the osteogenic differentiation of MSCs, with the MSCs cultured on the SC mesh stained more intensely for alizarin red than the RC mesh. Minimal alizarin red staining was detected from the MSCs cultured on RC or SC meshes in expansion media. And as expected, the meshes without seeded cells exhibited negligible non-specific absorption of the negatively charged alizarin red dye. The ability of the SC fibrous mesh to more readily support the attachment and osteogenic differentiation of MSCs than the uncharged RC mesh suggests a potential role of the charged sulfate residue in affecting the cellular fate of MSCs in vitro and in vivo. How such a chemical modification affects the multi-potency of MSCs, particularly osteogenesis, chondrogenesis and adipogenesis, in a temporally defined manner is the subject of on-going investigations.

Example 5

Figure 6:
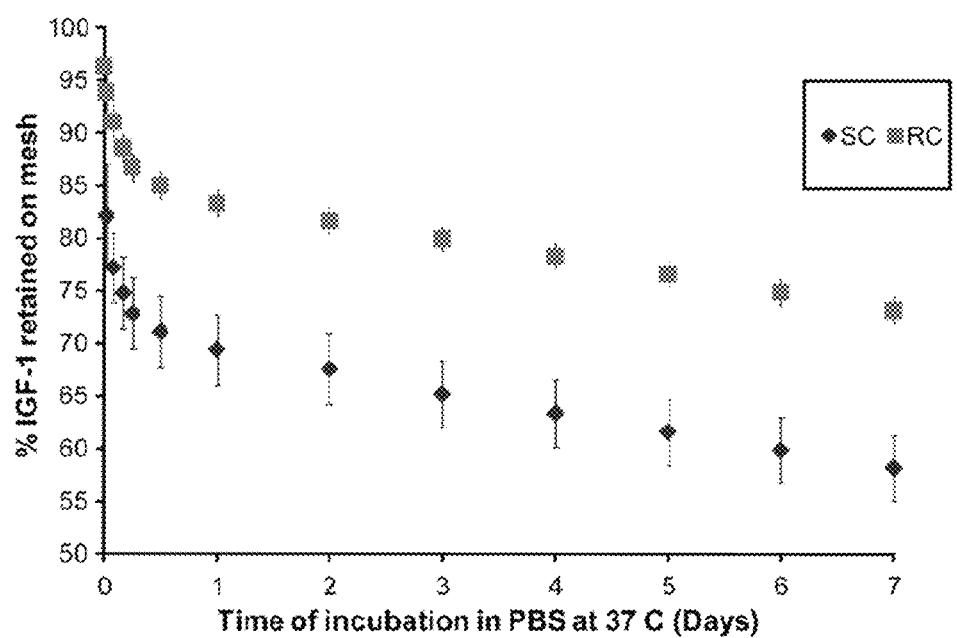
FIG. 6 shows: Sulfated cellulose (SC) and regenerated cellulose (RC) meshes release pre-absorbed IGF-1 in a sustained manner over a 7-day incubation in PBS (37° C., 5% $CO_2$). Quantitation carried out by ELISA.

To demonstrate the ability of RC and SC fibrous meshes to retain/release other protein therapeutics, the meshes were absorbed with a single dose of rhIGF-1 (R&D Systems, pI=8.59, 27-ng/cm$^2$) and incubated in PBS at 37° C. for 7 days. The rhIGF-1 released from the meshes over time was quantified by an enzyme-linked immunosorbent assay (ELISA, R&D Systems). Both meshes released pre-absorbed rhIGF-1 in a sustained manner over 7 days (FIG. 6). The RC mesh retained >70% of the protein after 7 days, while the SC mesh retained >55%.

Example 6

Figure 7:
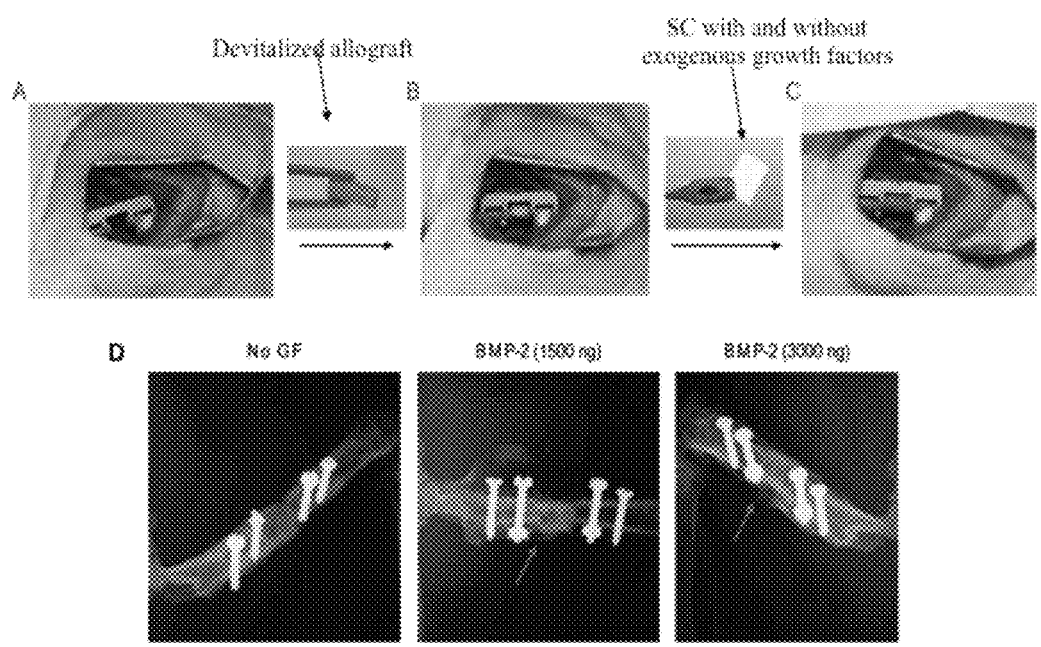
FIG. 7 shows: A-C: SC mesh can be wrapped around an allograft tight-fit within a 5-mm femoral segmental defect in a skeletally mature rat. D: At 8 weeks post-operation, x-ray radiography revealed varying levels of bony bridging (red arrows) over the femoral defects filled with devitalized allografts wrapped with SC mesh pre-loaded with 0 (no growth factor), 1500-ng, or 3000-ng rhBMP-2.
Figure 8:
FIG. 8 shows: 3-D reconstruction of the MicroCT scans of a 12-week explant showing robust new bone formation bridging over the allograft/SC mesh tight-fit within the 5-mm rat femoral segmental defect when a single dose of 3000 ng rhBMP-2 was pre-absorbed on the SC mesh prior to implantation.

To assess the ability of SC fibrous meshes to act as scaffolds and therapeutic delivery vehicles in vivo, the performance of SC fibrous meshes in augmenting bone allograft healing as a synthetic periosteum was examined. Structural bone allografts used in this study were aseptically harvested from rat femora with periosteum and bone marrow removed, followed by rinses in sterile PBS and 70% ethanol before being frozen for >24 hours at −80° C. for graft devitalization prior to use. SC meshes were used as 2-D scaffolds delivering rhBMP-2 (0 ng, 1500 ng or 3000 ng) and were wrapped around a devitalized bone allografts press-fit within the site of a 5-mm critical-size femoral defect in skeletally mature rats (SASCO SD rats, Charles River Laboratories; FIGS. 7A-7C). As shown by x-ray radiography (FIG. 7D), SC meshes pre-absorbed with a low-dose rhBMP-2 were able to promote varying degrees of bony callus bridging over the defects by 8 weeks. By 12 weeks, SC mesh pre-absorbed with 3000-ng of rhBMP-2 was shown to enable robust bony bridging over the bone allograft. As shown by microCT (FIG. 8), mature and recanalized bone bridged over the entire defect and spanned the allograft-cortical bone defect interface. The addition of other growth factor therapeutics and pluripotent bone marrow stromal cells to the mesh to further enhance the graft healing is under investigation.

Figure 9:
FIG. 9 shows: H&E staining of vital and scavenger organs retrieved from the rat 12 week after receiving allograft/SC/rhBMP-2 implant did not reveal any abnormality, supporting the general biocompatibility and safety of SC mesh combined with a single dose of 3000 ng rhBMP-2.
Figure 9:
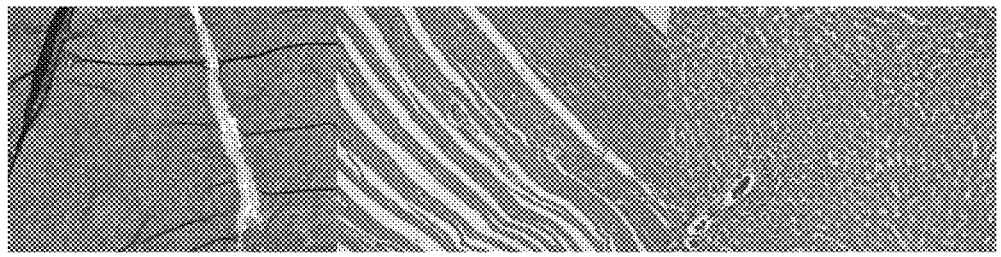

To examine the safety of the SC meshes in vivo, vital and scavenger organs were harvested from a rat 12 weeks after receiving an allograft wrapped with SC pre-absorbed with 3000-ng rhBMP-2 and examined grossly and histologically (FIG. 9). No remarkable systemic side-effects were observed, underscoring the biocompatibility of the SC mesh and its ability to safely deliver protein therapeutics in a localized manner.

In summary, using a combination of electrospinning, thermal-mechanical annealing, and sequential chemical modifications, water-stable sulfated cellulose fibrous mesh exhibiting good tensile mechanical strength was fabricated. The sulfated fibrous mesh exhibited better retention capacities for osteogenic growth factor rhBMP-2, and more readily supported the attachment and osteogenic differentiation of MSCs than the uncharged cellulose fibrous mesh. These fibrous meshes have great potential for bone tissue engineering applications.

Incorporation By Reference

References and citations to other documents, such as patents, patent applications, patent publications, journals, books, papers, web contents, have been made in this disclosure. All such documents are hereby incorporated herein by reference in their entirety for all purposes.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

What is claimed is:

1. A fibrous mesh of thermal-mechanically annealed cellulose that is subsequently oxidized and sulfated,
wherein the thermal-mechanical annealing is performed under a pressure in the range from about 10 MPa to about 500 MPa and at a temperature from about 60° C. to about 240° C.; and wherein
the fibrous mesh have thicknesses from about 10 µm to about 500 µm and comprise fibers from about 100 nm to about 20 µm in fiber diameter;
the fibrous mesh comprises fibers having a tensile elastic modulus from 2 MPa to 20 MPa and an ultimate tensile strength from 50 KPa to 1.0 MPa.

2. A biocompatible mesh composition, comprising:
fibrous sulfated cellulose, wherein the sulfated cellulose was obtained from thermal-mechanically annealed and subsequently chemically modified cellulose acetate; and
a therapeutic material absorbed on the fibrous sulfated cellulose,
wherein the thermal-mechanical annealing is performed under a pressure in the range from about 10 MPa to about 500 MPa and at a temperature from about 60° C. to about 240° C., wherein
the biocompatible mesh have thicknesses from about 10 µm to about 500 µm and comprise fibers from about 100 nm to about 20 µm in fiber diameter;
the biocompatible mesh comprises fibers having a tensile elastic modulus from 2 MPa to 20 MPa and an ultimate tensile strength from 50 KPa to 1.0 MPa.

3. The biocompatible mesh composition of claim 2, wherein the therapeutic material comprises a growth factor.

4. The biocompatible mesh composition of claim 3, wherein the growth factor is selected from isoforms of BMP (bone morphogenetic protein), VEGF (vascular endothelial growth factor), IGF (insulin-like growth factor), TGFbeta (transforming growth factor beta), FGF (fibroblast growth factor), RANKL (Receptor activator of nuclear factor kappa-B ligand), SDF (Stromal-derived factor), or TNFalpha (tumor necrosis factor alpha).

5. The biocompatible mesh composition of claim 3, wherein the growth factor is an osteogenic growth factor.

6. The biocompatible mesh composition of claim 2, wherein the therapeutic material comprises a bone marrow stromal cell (MSC).

7. The biocompatible mesh composition of claim 6, wherein the bone marrow stromal cell is present in the range from about 1000 to about 10,000,000 cells/cm$^2$.

8. The biocompatible mesh of claim 2, wherein the thermal-mechanically annealed and subsequently chemically modified cellulose acetate is obtained by:
electrospinning cellulose acetate to form cellulose acetate mesh;
thermal-mechanically annealing the electrospun cellulose acetate mesh;
deacetylating the annealed cellulose mesh;
oxidizing the deacetylated cellulose mesh to obtain aldehyde reactive functionalities; and
reacting the oxidized cellulose mesh with an amino-sulfate to obtain sulfated cellulose meshes.

9. A water-stable biocompatible fibrous mesh, prepared by the process comprising
electrospinning cellulose acetate to form cellulose acetate meshes;
thermal-mechanically annealing the electrospun cellulose acetate meshes; and
chemically modifying the annealed cellulose acetate meshes,
wherein the thermal-mechanical annealing is performed under a pressure in the range from about 10 MPa to about 500 MPa and at a temperature from about 60° C. to about 240° C., wherein
the water-stable biocompatible mesh have thicknesses from about 10 µm to about 500 µm and comprise fibers from about 100 nm to about 20 µm in fiber diameter;
the water-stable biocompatible mesh comprises fibers having a tensile elastic modulus from 2 MPa to 20 MPa and an ultimate tensile strength from 50 KPa to 1.0 MPa.

10. The water-stable biocompatible fibrous mesh of claim 9, wherein chemically modifying the annealed cellulose meshes comprises:
deacetylating the annealed cellulose meshes;
oxidizing the deacetylated cellulose meshes to obtain aldehyde reactive functionalities; and
reacting the oxidized cellulose meshes with an amino-sulfate to obtain sulfated cellulose meshes.

* * * * *